United States Patent
Maile et al.

(10) Patent No.: US 9,427,589 B2
(45) Date of Patent: Aug. 30, 2016

(54) LEADLESS CARDIAC PACEMAKER HAVING A SENSOR WITH A LOWER POWER MODE

(71) Applicant: Cardiac Pacemakers, Inc., St. Paul, MN (US)

(72) Inventors: Keith P. Maile, New Brighton, MN (US); Jeffrey E. Stahmann, Ramsey, MN (US); Michael J. Kane, Roseville, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 0 days.

(21) Appl. No.: 14/829,249

(22) Filed: Aug. 18, 2015

(65) Prior Publication Data

US 2016/0051823 A1 Feb. 25, 2016

Related U.S. Application Data

(60) Provisional application No. 62/040,649, filed on Aug. 22, 2014.

(51) Int. Cl.
*A61N 1/00* (2006.01)
*A61N 1/37* (2006.01)
(Continued)

(52) U.S. Cl.
CPC .......... *A61N 1/3708* (2013.01); *A61N 1/36514* (2013.01); *A61N 1/36521* (2013.01); *A61N 1/36564* (2013.01); *A61N 1/36571* (2013.01); *A61N 1/36578* (2013.01); *A61N 1/36585* (2013.01); *A61N 1/3756* (2013.01); *A61N 1/37217* (2013.01); *A61B 5/0538* (2013.01);
(Continued)

(58) Field of Classification Search
CPC ................... A61B 2562/0219; A61B 5/0538; A61B 5/1107; A61N 1/36514; A61N 1/36521; A61N 1/36564; A61N 1/36571; A61N 1/36578; A61N 1/36585; A61N 1/3708; A61N 1/37205; A61N 1/37217; A61N 1/3756
See application file for complete search history.

(56) References Cited

U.S. PATENT DOCUMENTS 7,937,148 B2 5/2011 Jacobson
8,571,678 B2 10/2013 Wang
(Continued)

FOREIGN PATENT DOCUMENTS

EP 503823 A2 11/2003
WO 2006086435 A3 8/2006
(Continued)

OTHER PUBLICATIONS

Notification of Transmittal of the International Search Report and the Written Opinion of the International Searching Authority, or the Declaration, Jan. 29, 2016, 15 pages.

*Primary Examiner* — George Manuel
(74) *Attorney, Agent, or Firm* — Seager, Tufte & Wickhem LLP

(57) ABSTRACT

A leadless cardiac pacemaker (LCP) configured to sense and pace a patient's heart includes a sensor configured to sense a parameter related to cardiac contractility of the patient's heart and a power management unit that is operatively coupled to the sensor. The power management unit is configured to place the sensor in a higher power sense mode during times when sensing the parameter related to cardiac contractility is desired and to place the sensor in a lower power mode during times when sensing the parameter related to cardiac contractility is not desired.

20 Claims, 12 Drawing Sheets

(51) Int. Cl.
*A61N 1/365* (2006.01)
*A61N 1/372* (2006.01)
*A61N 1/375* (2006.01)
*A61B 5/053* (2006.01)
*A61B 5/11* (2006.01)

(52) U.S. Cl.
CPC ...... *A61B 5/1107* (2013.01); *A61B 2562/0219* (2013.01); *A61N 1/37205* (2013.01)

(56) References Cited

U.S. PATENT DOCUMENTS

| | | |
|---|---|---|
| 8,744,572 B1 | 6/2014 | Greenhut et al. |
| 9,072,913 B2 | 7/2015 | Jacobson |
| 2006/0178586 A1* | 8/2006 | Dobak, III ............... A61B 5/02 600/508 |
| 2006/0178589 A1* | 8/2006 | Dobak, III ............... A61B 5/02 600/514 |
| 2011/0208260 A1 | 8/2011 | Jacobson |
| 2014/0214104 A1 | 7/2014 | Greenhut et al. |
| 2015/0105836 A1 | 4/2015 | Bonner et al. |
| 2015/0173655 A1 | 6/2015 | Demmer et al. |
| 2015/0217119 A1 | 8/2015 | Nikolski et al. |
| 2015/0328459 A1 | 11/2015 | Chin et al. |
| 2016/0015322 A1 | 1/2016 | Anderson et al. |
| 2016/0023000 A1 | 1/2016 | Cho et al. |

FOREIGN PATENT DOCUMENTS

| | | |
|---|---|---|
| WO | 2006113659 A1 | 10/2006 |
| WO | 2007075974 A2 | 7/2007 |
| WO | 2012054102 A1 | 4/2012 |

* cited by examiner

LEADLESS CARDIAC PACEMAKER HAVING A SENSOR WITH A LOWER POWER MODE

CROSS REFERENCE TO RELATED APPLICATIONS

This application claims the benefit of U.S. Provisional Patent Application Ser. No. 62/040,649 filed on Aug. 22, 2014, the disclosures of each incorporated herein by reference.

TECHNICAL FIELD

The present disclosure generally relates to implantable medical devices and more particularly to implantable leadless cardiac pacemakers.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices that are configured to communicate information between the devices.

SUMMARY

The present disclosure generally relates to implantable medical devices and more particularly to implantable leadless cardiac pacemakers.

In a first example, a leadless cardiac pacemaker (LCP) for sensing and pacing a patient's heart includes a sensor that is configured to sense a parameter related to cardiac contractility of the patient's heart. A power management unit is operatively coupled to the sensor. The power management unit is configured to place the sensor in a higher power sense mode during times when sensing the parameter related to cardiac contractility is desired, and to place the sensor in a lower power mode during times when sensing the parameter related to cardiac contractility is not desired.

Alternatively, or additionally, and in a second example, the sensor of the first example includes an accelerometer.

Alternatively, or additionally, and in a third example, the sensor of the first example includes one or more of an acoustic sensor, an impedance sensor, a flow sensor and a pressure sensor.

Alternatively, or additionally, and in a fourth example, the power management unit of any of the first through third examples turns the sensor on in the higher power sense mode and turns the sensor off in the lower power mode.

Alternatively, or additionally, and in a fifth example, the sensor of any of the first through fourth examples consumes power in the higher power sense mode but does not consume power in the lower power mode.

Alternatively, or additionally, and in a sixth example, the sensor of any of the first through fourth examples consumes power in both the higher power sense mode and the lower power mode.

Alternatively, or additionally, and in a seventh example, the parameter related to cardiac contractility of the patient's heart of any of the first through sixth examples is related to the peak endocardial acceleration (PEA) of the heart. The peak endocardial acceleration (PEA) is an indication of how well the heart is pumping blood.

Alternatively, or additionally, and in an eighth example, the power management system of any of the first through seventh examples receives a cardiac cycle marker, places the sensor in the higher power sense mode during a detection window that starts a predetermined time after the cardiac cycle marker and places the sensor in the lower power mode after the detection window.

Alternatively, or additionally, and in a ninth example, the cardiac cycle marker of the eighth examples includes one or more of a detected R-wave, a pace event and a detected heart sound.

Alternatively, or additionally, and in a tenth example, the power management system of any of the eighth through ninth examples is configured to place the sensor in the higher power sense mode N times for every M cardiac cycle markers, where N is less than M.

Alternatively, or additionally, and in an eleventh example, N and M of the tenth example are dependent upon a patient activity level.

Alternatively, or additionally, and in a twelfth example, the leadless cardiac pacemaker (LCP) of any of the first through eleventh examples further includes a pacing module for pacing the heart at a pacing rate, wherein the pacing rate is dependent, at least in part, on the sensed parameter related to cardiac contractility of the patient's heart.

In a thirteenth example, a system includes a leadless cardiac pacemaker (LCP) and an external sensor, remote from the leadless cardiac pacemaker, for detecting a cardiac cycle maker and communicating the marker via conducted communication to the leadless cardiac pacemaker (LCP). The leadless cardiac pacemaker (LCP) includes a housing and an accelerometer disposed within the housing. A controller is configured to activate the accelerometer in response to a detected cardiac cycle marker. The leadless cardiac pacemaker includes two or more electrodes for receiving conducted communication signals emanating from outside of the housing and a receiver coupled to the two or more electrodes for receiving a communication via conducted communication from outside the housing.

Alternatively, or additionally, and in a fourteenth example, the external sensor of the thirteenth example includes a pressure sensor.

Alternatively, or additionally, and in fifteenth example, the external sensor of the thirteenth example includes a flow sensor.

Alternatively, or additionally, and in sixteenth example, the external sensor of the thirteenth example includes an impedance sensor.

In a seventeenth example, a method of monitoring heart activity using a leadless cardiac pacemaker (LCP) having an accelerometer, a battery and a power management unit includes detecting a cardiac cycle marker. In response to the detected cardiac cycle marker, the accelerometer is activated in order to obtain a measure related to a peak endocardial acceleration (PEA) value. The accelerometer is deactivated after obtaining the measure related to the peak endocardial acceleration (PEA) value in order to conserve battery power in the battery.

Alternatively, or additionally, and in an eighteenth example, the method of the seventeenth example further includes providing pacing signals.

Alternatively, or additionally, and in a nineteenth example, the method of the eighteenth example further includes adjusting the pacing signals based, at least in part, on the obtained measure related to a peak endocardial acceleration (PEA) value.

Alternatively, or additionally, and in a twentieth example, the method of any of the seventeenth through nineteenth examples in which detecting a cardiac cycle marker includes detecting an R-wave.

Alternatively, or additionally, and in a twenty first example, the power management unit of the seventeenth through twentieth examples activates the accelerometer N times for each M detected cardiac cycle markers, where N is less than M.

Alternatively, or additionally, and in a twenty second example, the method of the twenty first example further includes adjusting N and M in accordance with patient activity.

Alternatively, or additionally, and in a twenty third example, the power management unit of any of the seventeenth through twenty second examples is configured to activate the accelerometer in response to a pace event.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
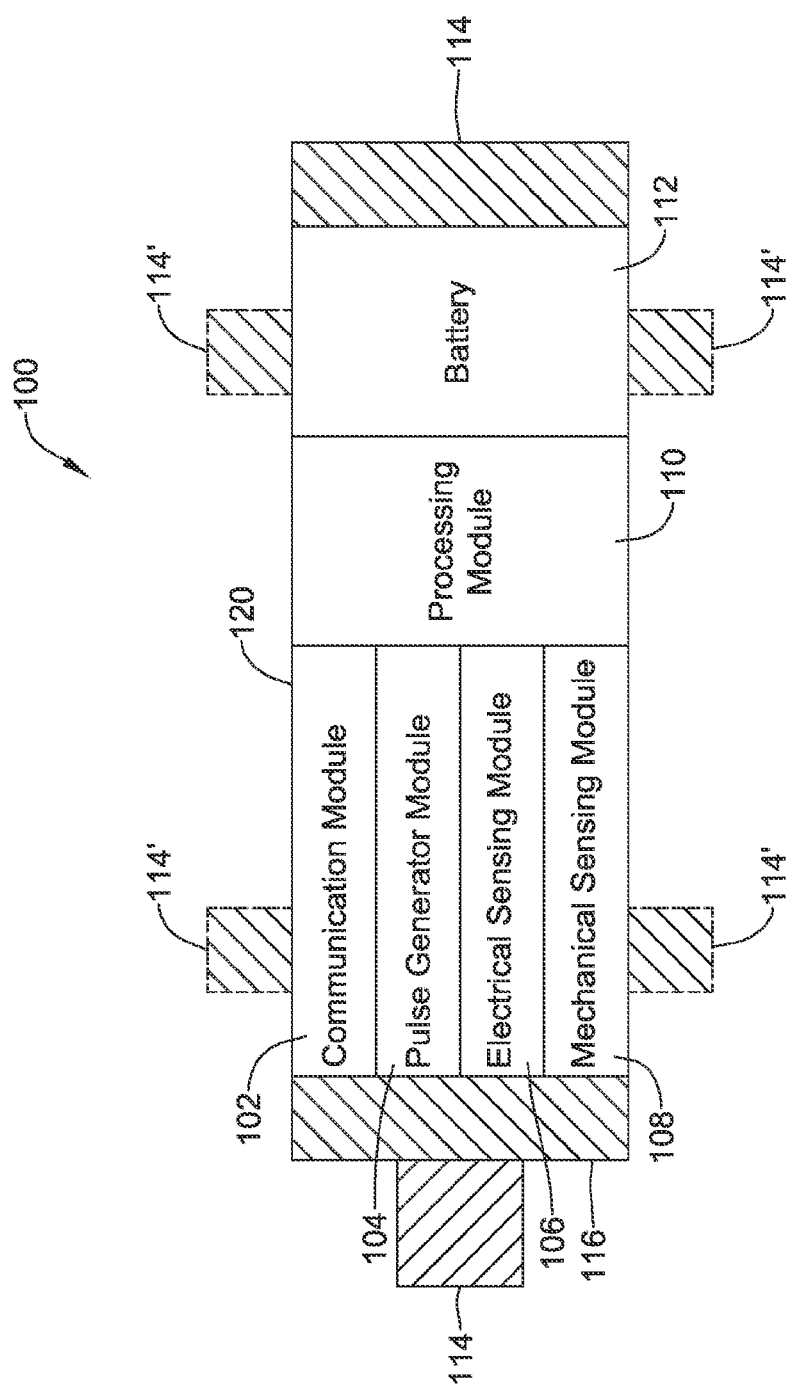
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to determine occurrences of such cardiac abnormalities or arrhythmias and deliver one or more types of electrical stimulation therapy to patient's hearts may help to terminate or alleviate such cardiac conditions.

FIG. 1 depicts an exemplary leadless cardiac pacemaker (LCP) that may be implanted into a patient and may operate to prevent, control, or terminate cardiac arrhythmias in patients, for example by appropriately employing one or more therapies (e.g. anti-tachycardia pacing (ATP) therapy, cardiac resynchronization therapy (CRT), bradycardia therapy, defibrillation pulses, or the like). As can be seen in FIG. 1, LCP 100 may be a compact device with all components housed within LCP 100 or directly on housing 120. In the example shown in FIG. 1, LCP 100 may include a communication module 102, a pulse generator module 104, an electrical sensing module 106, a mechanical sensing module 108, a processing module 110, a battery 112, and electrodes 114. LCP 100 may include more or less modules, depending on the application.

Communication module 102 may be configured to communicate with devices such as sensors, other medical devices, and/or the like, that are located externally to LCP 100. Such devices may be located either external or internal to the patient's body. Irrespective of the location, external devices (i.e. external to the LCP 100 but not necessarily external to the patient's body) can communicate with LCP 100 via communication module 102 to accomplish one or more desired functions. For example, LCP 100 may communicate information, such as sensed electrical signals, data, instructions, messages, etc., to an external medical device through communication module 102. The external medical device may use the communicated signals, data, instructions and/or messages to perform various functions, such as determining occurrences of arrhythmias, delivering electrical stimulation therapy, storing received data, and/or performing any other suitable function. LCP 100 may additionally receive information such as signals, data, instructions and/or messages from the external medical device through communication module 102, and LCP 100 may use the received signals, data, instructions and/or messages to perform various functions, such as determining occurrences of arrhythmias, delivering electrical stimulation therapy, storing received data, and/or performing any other suitable function. Communication module 102 may be configured to use one or more methods for communicating with external devices. For example, communication module 102 may communicate via radiofrequency (RF) signals, inductive coupling, optical signals, acoustic signals, conducted communication signals, and/or any other signals suitable for communication.

In the example shown in FIG. 1, pulse generator module 104 may be electrically connected to electrodes 114. In some examples, LCP 100 may additionally include electrodes 114'. In such examples, pulse generator 104 may also be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. Alternatively, or additionally, pulse generator 104 may include one or more capacitors, and pulse generator 104 may charge the one or more capacitors by drawing energy from battery 112. Pulse generator 104 may then use the energy of the one or more capacitors to deliver the generated electrical stimulation signals via electrodes 114 and/or 114'. In at least some examples, pulse generator 104 of LCP 100 may include switching circuitry to selectively connect one or more of electrodes 114 and/or 114' to pulse generator 104 in order to select which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, LCP 100 may not include a pulse generator 104. For example, LCP 100 may be a diagnostic only device. In such examples, LCP 100 may not deliver electrical stimulation therapy to a patient. Rather, LCP 100 may collect data about cardiac electrical activity and/or physiological parameters of the patient and communicate such data and/or determinations to one or more other medical devices via communication module 102.

In some examples, LCP 100 may include an electrical sensing module 106, and in some cases, a mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. The cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical/chemical parameters of the patient. Both electrical sensing module 106 and mechanical sensing module 108 may be connected to a processing module 110, which may provide signals representative of the sensed mechanical parameters. Although described with respect to FIG. 1 as separate sensing modules, in some cases, electrical sensing module 206 and mechanical sensing module 208 may be combined into a single sensing module, as desired.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 through short connecting wires such that electrodes 114/114' are not directly secured relative to housing 120. In examples where LCP 100 includes one or more electrodes 114', electrodes 114' may in some cases be disposed on the sides of LCP 100, which may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other parts of the LCP 100.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases, types of arrhythmias. Based on any determined arrhythmias, processing module 110 may control pulse generator module 104 to generate electrical stimulation in accordance with one or more therapies to treat the determined arrhythmia(s). Processing module 110 may further receive information from communication module 102. In some examples, processing module 110 may use such received information to help determine whether an arrhythmia is occurring, determine a type of arrhythmia, and/or to take particular action in response to the information. Processing module 110 may additionally control communication module 102 to send/receive information to/from other devices.

In some examples, processing module 110 may include a pre-programmed chip, such as a very-large-scale integration (VLSI) chip and/or an application specific integrated circuit (ASIC). In such embodiments, the chip may be pre-programmed with control logic in order to control the operation of LCP 100. By using a pre-programmed chip, processing module 110 may use less power than other programmable circuits (e.g. general purpose programmable microprocessors) while still being able to maintain basic functionality, thereby potentially increasing the battery life of LCP 100. In other examples, processing module 110 may include a programmable microprocessor. Such a programmable microprocessor may allow a user to modify the control logic of LCP 100 even after implantation, thereby allowing for greater flexibility of LCP 100 than when using a pre-programmed ASIC. In some examples, processing module 110 may further include a memory, and processing module 110 may store information on and read information from the memory. In other examples, LCP 100 may include a separate memory (not shown) that is in communication with processing module 110, such that processing module 110 may read and write information to and from the separate memory.

Battery 112 may provide power to the LCP 100 for its operations. In some examples, battery 112 may be a non-rechargeable lithium-based battery. In other examples, a non-rechargeable battery may be made from other suitable materials, as desired. Because LCP 100 is an implantable device, access to LCP 100 may be limited after implantation. Accordingly, it is desirable to have sufficient battery capacity to deliver therapy over a period of treatment such as days, weeks, months, years or even decades. In some instances, battery 110 may a rechargeable battery, which may help increase the useable lifespan of LCP 100. In still other examples, battery 110 may be some other type of power source, as desired.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 2:
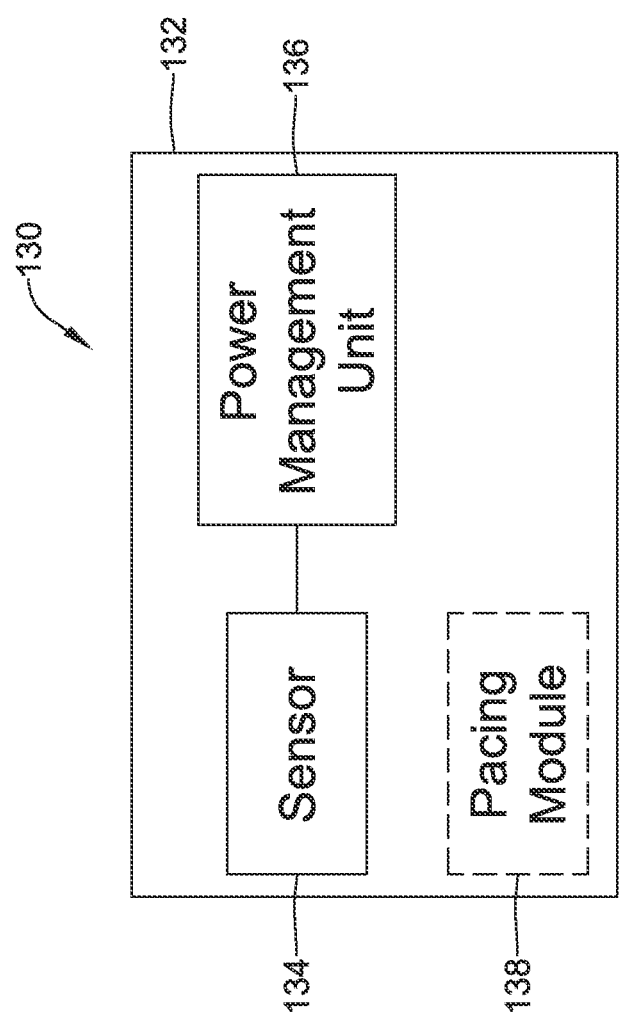
FIG. 2 is a schematic block diagram of an illustrative leadless cardiac pacemaker (LCP) according to one example of the present disclosure.

FIG. 2 depicts an example of another leadless cardiac pacemaker (LCP) 130. In some embodiments, LCP 130 may include many of the features and elements, including various modules, illustrated in FIG. 1 with respect to LCP 100. LCP 130 includes a housing 132. Among other features, LCP 130 includes a sensor 134 and a power management unit 136 that is operably coupled to the sensor 134. Sensor 134 may take a variety of different forms, but in some embodiments may be a sensor that is configured to sense a parameter related to cardiac contractility of the patient's heart. For example, sensor 134 may be or include an accelerometer. In some embodiments, sensor 134 may include one or more of an acoustic sensor, an impedance sensor, a flow sensor, a pressure sensor and/or any other suitable sensor.

In some embodiments, the parameter related to cardiac contractility of the patient's heart may include but not be limited to the Peak Endocardial Acceleration (PEA) of the patient's heart. The PEA value is an indication of how hard the ventricle is contracting, and thus may provide useful information of how well the heart is functioning. It will be appreciated that in some embodiments, sensor 134 may be manifested within mechanical sensing module 108 (FIG. 1). In some embodiments, power management unit 136 may be manifested within processing module 110 (FIG. 1).

Power management unit 136 may be configured to help reduce power consumption within LCP 130. In some embodiments, power management unit 136 may be configured to place sensor 134 into a higher power sense mode during times when sensing the parameter related to cardiac contractility is desired, and may place sensor 134 into a lower power mode during times when sensing the parameter related to cardiac contractility is not desired. In some embodiments, power management unit 136 turns on sensor 134 in the higher power sense mode and turns off sensor 134 in the lower power mode. In some embodiments, sensor 134 consumes power in the higher power sense mode but does not consume power in the lower power mode. In some embodiments, sensor 134 consumes power in both the higher power sense mode and the lower power mode, but consumes less power in the lower power mode.

In some embodiments, power management unit 136 receives a cardiac cycle marker, which can be obtained from a module within LCP 130, such as a sensor within mechanical sensing module 108 or electrical sensing module 106 (illustrated in FIG. 1) or from another device external to LCP 130. Once power management unit 136 receives the cardiac cycle marker, sensor 134 is placed into its higher power sense mode during a detection window that starts at or a predetermined time after the cardiac cycle marker. After the detection window, sensor 134 is placed into its lower power mode.

The detection window may have any suitable duration, such as 300 ms, 200 ms, 150 ms, 50 ms, 30 ms, 20 ms, 10 ms or less. In some embodiments, for example, the detection window may have a duration ranging from 10 ms to 300 ms, or 20 ms to 200 ms, or 30 ms to 150 ms. Also, the detection window may start a predetermined time after receipt of the cardiac cycle marker, such as after 0 ms, 5 ms, 10 ms, 20 ms, 30 ms, 50 ms, 100 ms, 200 ms, 300 ms, or more. A cardiac cycle marker may be, for example, one or more of a detected R-wave, a detected heart sound, a pace event, and/or any other suitable cardiac cycle marker. In some cases, a detected heart sound, or "lub dub", results from the heart valves closing and may be detected acoustically and/or via frequency by an accelerometer.

In some embodiments, sensor 134 may be disabled after a predetermined amount of time, such as for example 150 ms, after the cardiac cycle marker. In some embodiments, sensor 134 may be disabled after a predetermined amount of time that may, for example, range from 100 to 200 ms. In some embodiments, the predetermined amount of time may vary in accordance with the heart rate. In some embodiments, the starting time and/or duration of the detection window may vary, depending on whether the cardiac cycle marker is or indicates a paced event or a sensed event. It will be appreciated that power management unit 136 may implement an algorithm that runs periodically and adjusts detection window starting times and/or durations as appropriate. In some embodiments, power management unit 136 may implement an algorithm that disables sensor 134 after a particular amount of time below a desired threshold. For example, sensor 134 may be disabled 50 ms after a measured parameter such as PEA has dropped below a threshold. The threshold may, for example, be a particular percentage such as 50 percent of a maximum measured PEA.

Figure 11:
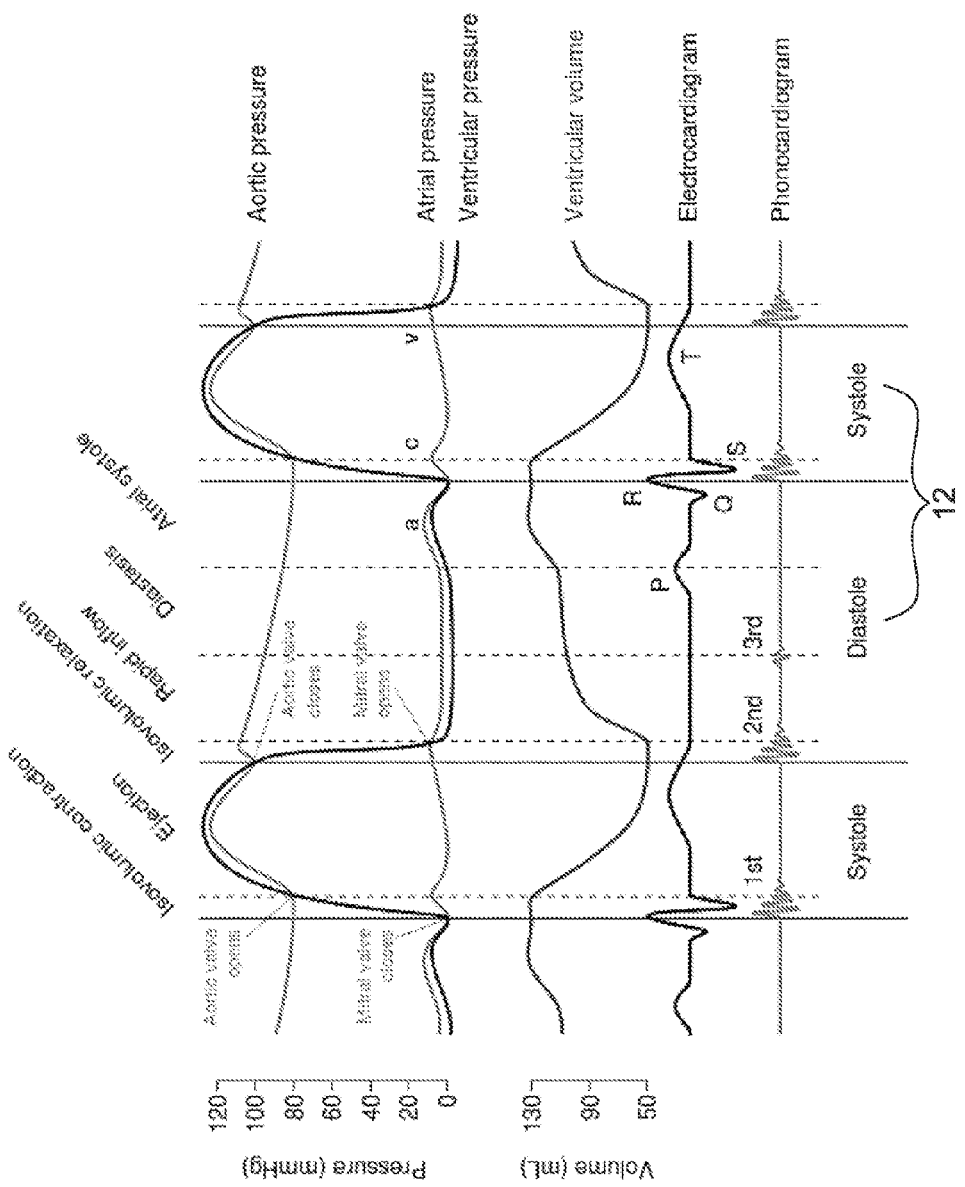
FIG. 11 is a graph providing a pressure curve.
Figure 12:
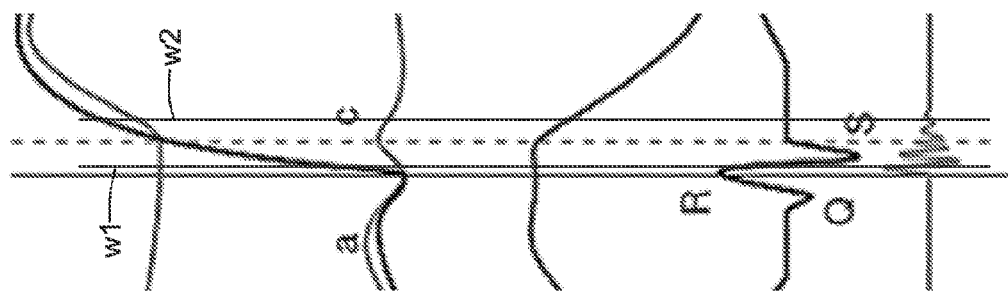
FIG. 12 is an enlarged portion of the graph of FIG. 11.

The detection window may be demonstrated with reference to FIG. 11, which is a pressure curve that illustrates several cardiac-related pressures, including ventricular pressure. FIG. 12 is an enlarged portion of FIG. 11, illustrating a portion of interest. A detection window is indicated by a first line W1 and a second line W2. It can be seen that first line W1 is positioned just after the initiation of the R-wave and second line W2 is positioned a short period of time later and is positioned such that the maximum change in pressure per time, dP/dt, occurs during the detection window.

In some embodiments, power management unit 136 places sensor 134 into the higher power sense mode every time a cardiac cycle marker is received. In some embodiments, in order to further conserve battery power, power management unit 136 may place sensor 134 into the higher power sense mode less than every time a cardiac cycle marker is received. For example, in some embodiments, power management unit 136 may place sensor 134 into the higher power sense mode "N" times for every "M" received cardiac cycle markers. As an illustrative but non-limiting example, N equals one and M equals 5, meaning that sensor 134 is placed into the higher power sense mode once for each five received cardiac cycle markers. In some embodiments, N and M may be dependent upon a patient activity level, and/or on the patient's perceived health. For example, if LCP 130 senses an increased heart rate indicating increased patient activity, power management unit 136 may set N closer to M. In another example, if LCP 130 senses irregularities in the patient's heart beat, power management unit 136 may set N closer to M while N may be set lower relative to M when LCP 130 does not sense irregularities or other issues in the patient's heart beat.

In some embodiments, and with reference to FIG. 2, LCP 130 may include a pacing module 138. In some embodiments, pacing module 138 may be manifested within pulse generator module 104 (FIG. 1). If appropriate, pacing module 138 may pace the patient's heart at a pacing rate that depends, at least in part, on the sensed parameter related to cardiac contractility. For example, pacing module 138 may pace at a relatively higher pacing rate if the sensed parameter indicates a higher Peak Endocardial Acceleration (PEA), and may pace at a relatively lower pacing rate if the sensed parameter indicates a lower Peak Endocardial Acceleration (PEA).

Figure 3:
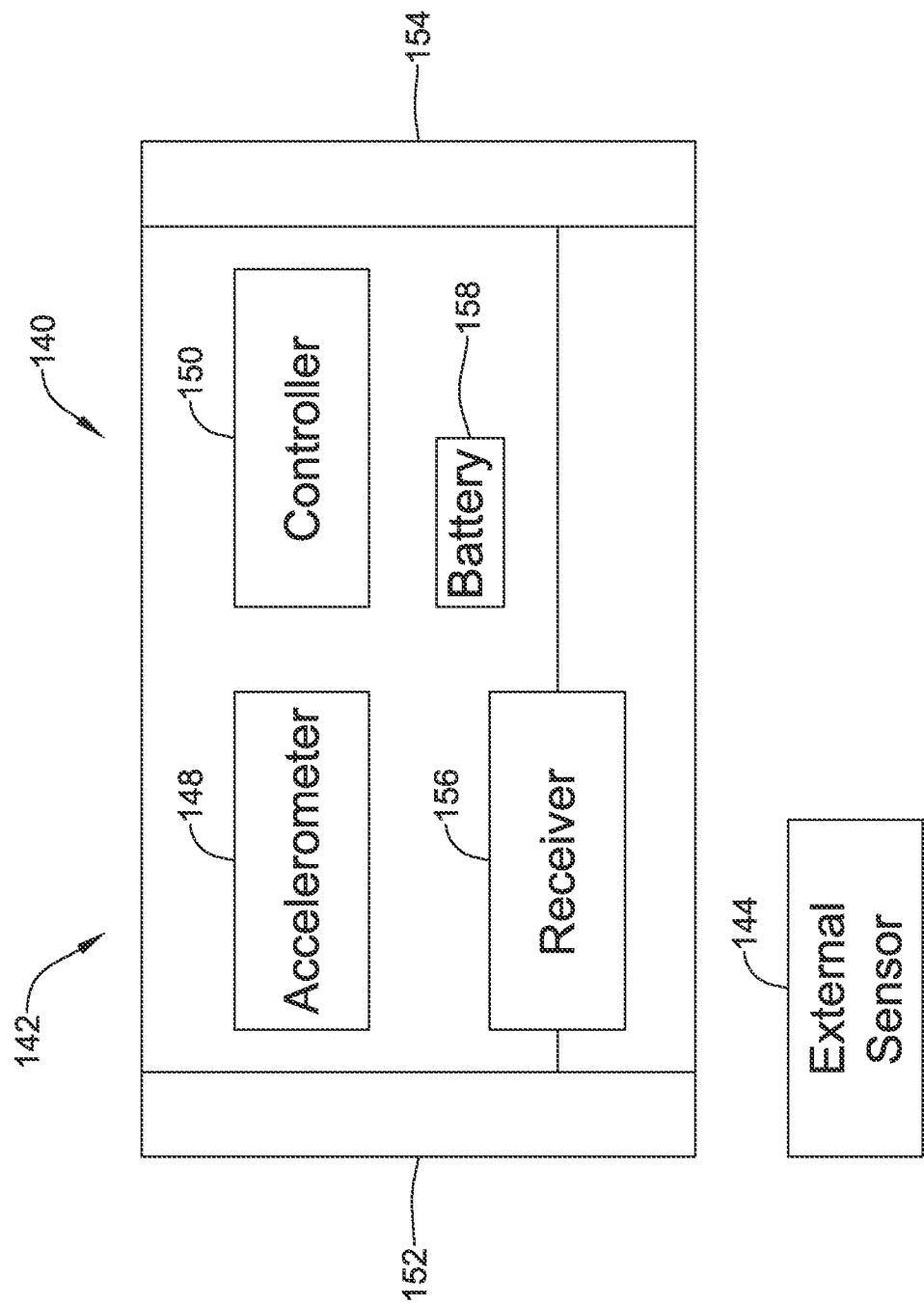
FIG. 3 is a schematic block diagram of an illustrative leadless cardiac pacemaker (LCP) according to one example of the present disclosure.

FIG. 3 provides an illustration of a system 140 that includes a leadless cardiac pacemaker (LCP) 142 and an external device 144. LCP 142 may include many of the features and modules described with respect to LCP 100 (FIG. 1) and LCP 130 (FIG. 2). The illustrative LCP 142 includes a housing 146 and an accelerometer 148 that is disposed within housing 146. A controller 150 is configured to activate accelerometer in response to a detected cardiac cycle marker. LCP 142 includes two or more electrodes 152, 154 that are configured for receiving conducted communication signals emanating from outside of housing 146. In some embodiments, the communication signals emanate from external device 144. LCP 142 includes a receiver 156 that is coupled to electrodes 152, 154 for receiving a communication via conducted communication from outside housing 146. The illustrative LCP 142 also includes a battery 158.

External device 144 may be internal to the patient, but exterior to LCP 142. In some embodiments, external device 144 may be external to the patient. External device 144 may include one or more of an electrical (ECG) sensor, a pressure sensor, a flow sensor, an impedance sensor and/or any other suitable sensor. In some embodiments, external device 144 detects a cardiac cycle marker and communicates the detected cardiac cycle marker via conducted communication to LCP 142. As noted, cardiac cycle markers may include but are not limited to a detected R-wave, a detected heart sound and/or a pace event to name a few.

Figure 4:
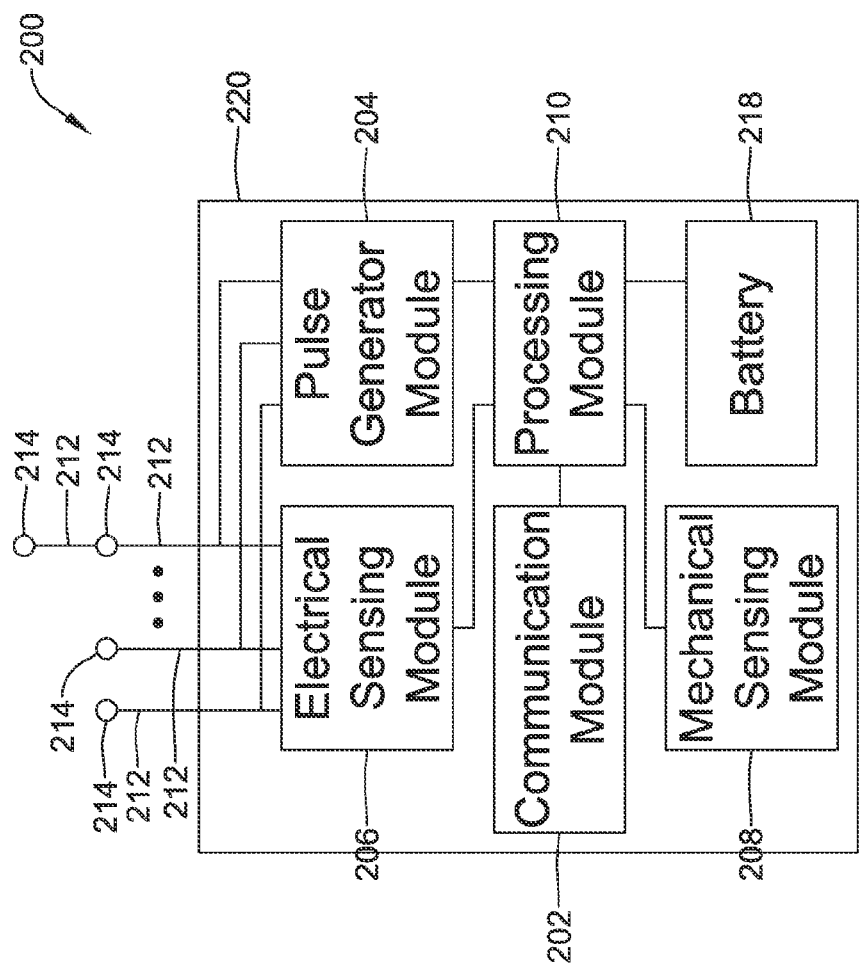
FIG. 4 is a schematic block diagram of another illustrative medical device that may be used in conjunction with the LCPs of FIGS. 1-3.

FIG. 4 depicts an example of another medical device (MD) 200, which may be used in conjunction with LCP 100 (FIG. 1), LCP 130 (FIG. 2) and/or LCP 142 (FIG. 3) in order to detect and/or treat cardiac arrhythmias and other heart conditions. In the example shown, MD 200 may include a communication module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. In some examples, however, MD 200 may have a larger volume within housing 220. In such examples, MD 200 may include a larger battery and/or a larger processing module 210 capable of handling more complex operations than processing module 110 of LCP 100.

While it is contemplated that MD 200 may be another leadless device such as shown in FIG. 1, in some instances MD 200 may include leads such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212, and in some cases at various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals and delivery the signals to the patient's heart (either directly or indirectly).

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more mechanical/chemical parameters of the heart and/or patient. In some examples, one or more of the sensors may be located on leads 212, but this is not required. In some examples, one or more of the sensors may be located in housing 220.

While not required, in some examples, MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and may include skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin). In such examples, MD 200 may be configured to deliver various types of electrical stimulation therapy, including, for example, defibrillation therapy.

Figure 5:
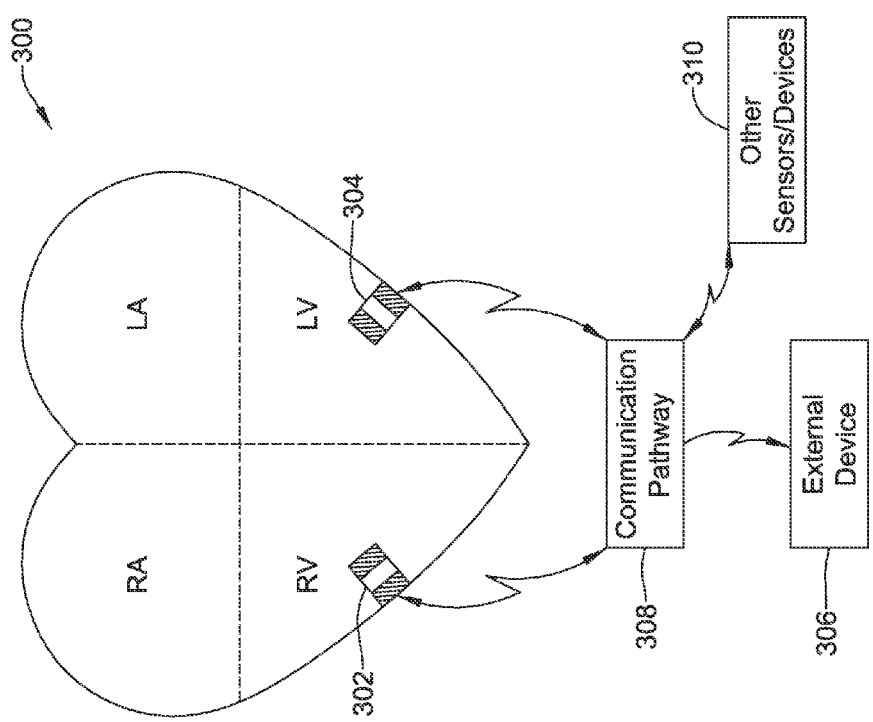
FIG. 5 is a schematic diagram of an exemplary medical system that includes multiple LCPs and/or other devices in communication with one another.

FIG. 5 illustrates an example of a medical device system and a communication pathway through which multiple medical devices 302, 304, 306, and/or 310 may communicate. In the example shown, medical device system 300 may include LCPs 302 and 304, external medical device 306, and other sensors/devices 310. External device 306 may be any of the devices described previously with respect to MD 200. Other sensors/devices 310 may also be any of the devices described previously with respect to MD 200. In some instances, other sensors/devices 310 may include a sensor, such as an accelerometer or blood pressure sensor, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. It is contemplated that communication pathway 308 may communicate using RF signals, inductive coupling, optical signals, acoustic signals, or any other signals suitable for communication. Additionally, in at least some examples, device communication pathway 308 may comprise multiple signal types. For instance, other sensors/device 310 may communicate with external device 306 using a first signal type (e.g. RF communication) but communicate with LCPs 302/304 using a second signal type (e.g. conducted communication). Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, communication pathway 308 may include conducted communication. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 6:
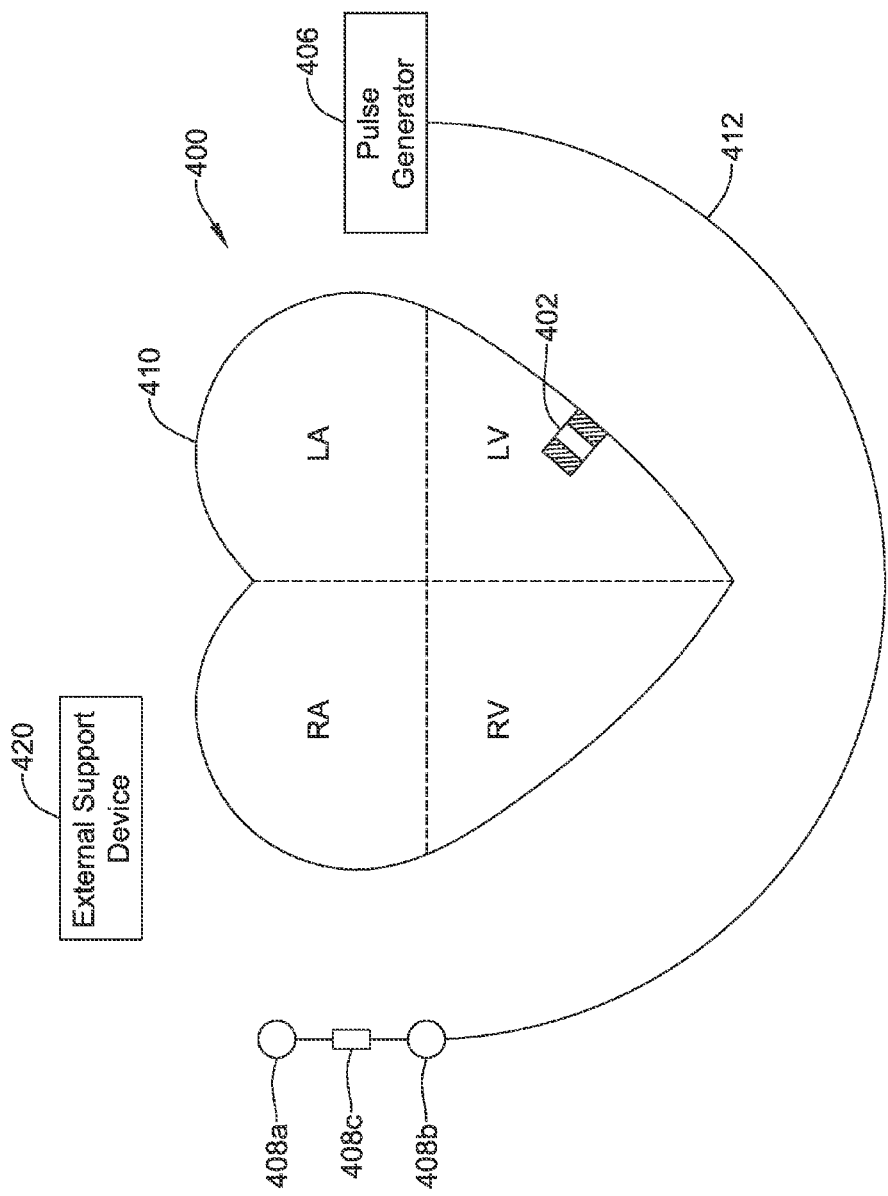
FIG. 6 is a schematic diagram of a system including an LCP and another medical device, in accordance with yet another example of the present disclosure.
Figure 7:
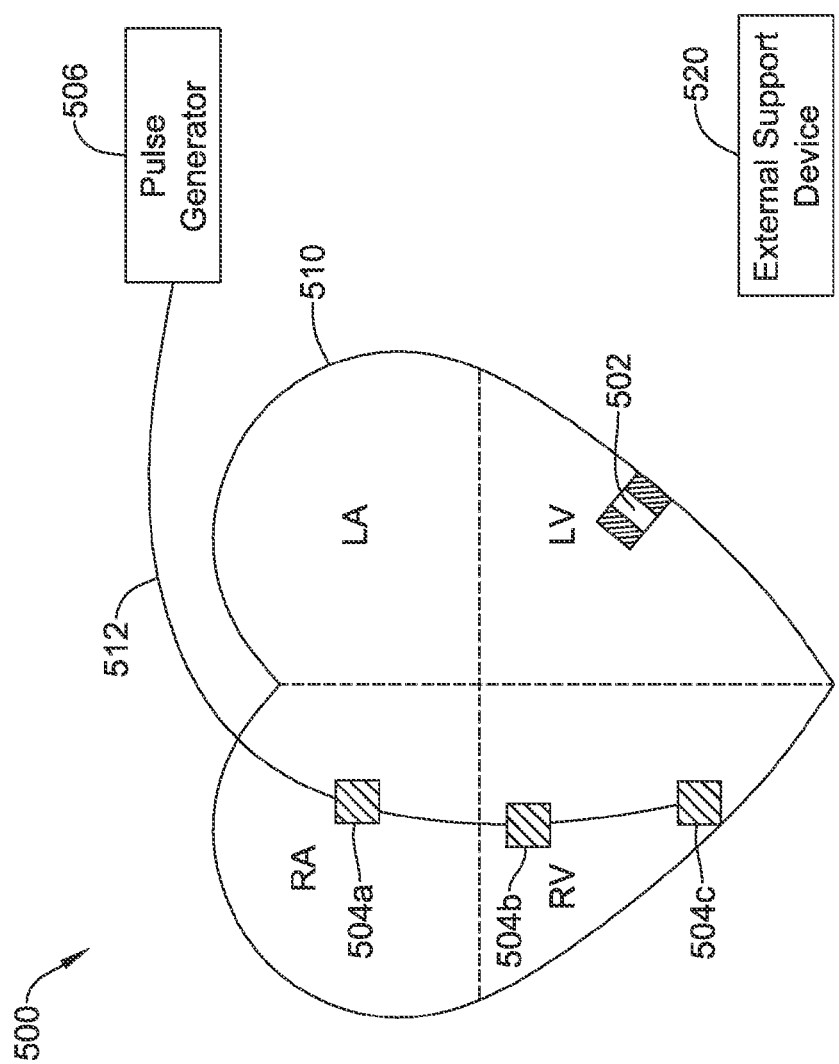
FIG. 7 is a schematic diagram of a system including an LCP and another medical device, in accordance with another example of the present disclosure.

FIGS. 6 and 7 show illustrative medical device systems that may be configured to operate according to techniques disclosed herein. In FIG. 6, an LCP 402 is shown fixed to the interior of the left ventricle of the heart 410, and a pulse generator 406 is shown coupled to a lead 412 having one or more electrodes 408*a*-408*c*. In some cases, the pulse generator 406 may be part of a subcutaneous implantable cardioverter-defibrillator (S-ICD), and the one or more electrodes 408*a*-408*c* may be positioned subcutaneously adjacent the heart. In some cases, the LCP 402 may communicate with the subcutaneous implantable cardioverter-defibrillator (S-ICD). In some cases, the LCP 302 may be in the right ventricle, right atrium or left atrium of the heart, as desired. In some cases, more than one LCP 302 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 7, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be via a communication module.

FIGS. 6-7 only illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 406 or 506, with at least one LCP capable of delivering defibrillation therapy. In yet other examples, the configuration or placement of the medical devices, leads, and/or electrodes may be different from those depicted in FIGS. 6 and 7. Accordingly, it should be recognized that numerous other medical device systems, different from those depicted in FIGS. 6 and 7, may be operated in accordance with techniques disclosed herein. As such, the examples shown in FIGS. 6 and 7 should not be viewed as limiting in any way.

Figure 8:
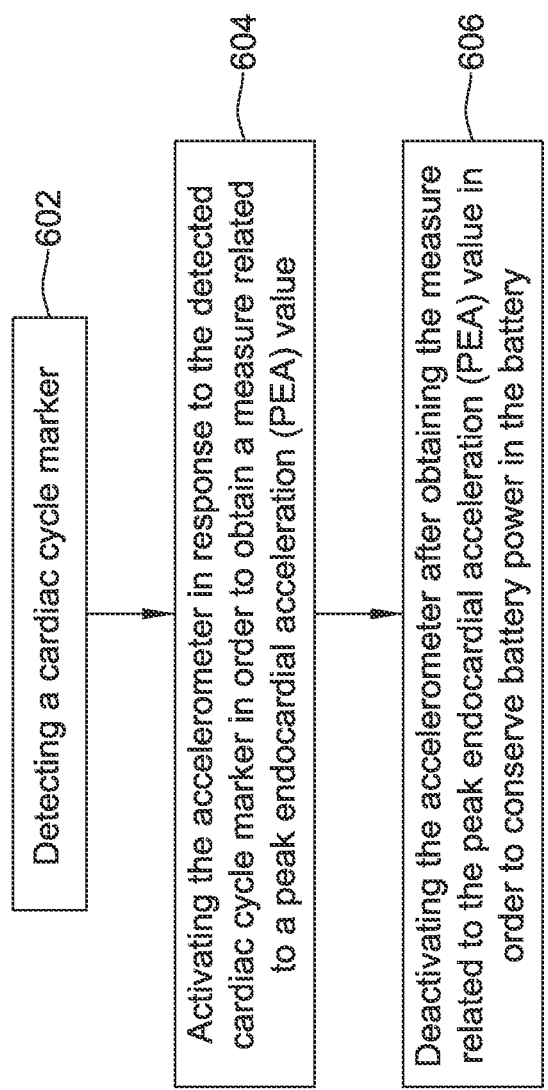
FIG. 8 is a flow diagram of an illustrative method that may be implemented by a medical device such as those illustrated in FIGS. 1-7.

FIG. 8 is a flow diagram showing an illustrative method that may be carried out using an LCP having an accelerometer, a battery and a power management unit. LCP 142 (FIG. 3) provides an illustrative but non limiting example of an LCP including an accelerometer (accelerometer 148), a battery (battery 158) and a power management unit (manifested within controller 150). As indicated at block 602, a cardiac cycle marker is detected. The cardiac cycle marker may be detected in any suitable manner. The accelerometer (such as accelerometer 148) is activated in response to the detected cardiac cycle marker in order to obtain, for example, a measured related to a peak endocardial acceleration (PEA) value as generally noted at block 604. The accelerometer is deactivated after obtaining the measure related to the peak endocardial acceleration (PEA) value in order to conserve battery power in the battery, as generally noted at block 606.

Figure 9:
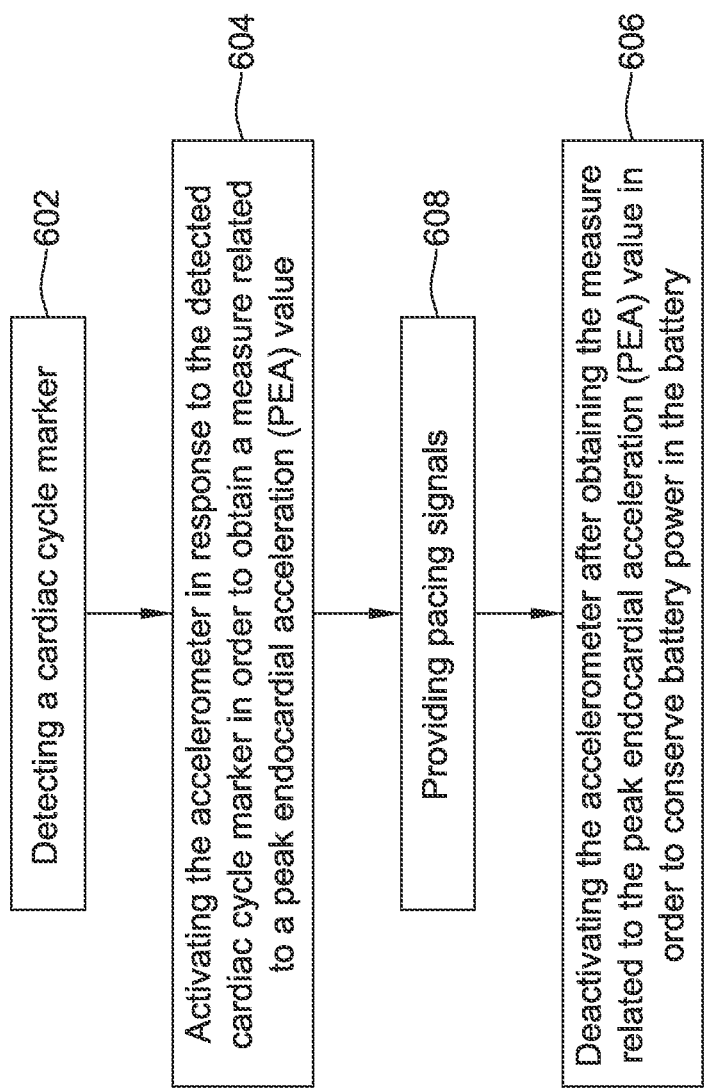
FIG. 9 is a flow diagram of an illustrative method that may be implemented by a medical device such as those illustrated in FIGS. 1-7.

FIG. 9 is a flow diagram showing an illustrative method that may be carried out using an LCP having an accelerometer, a battery and a power management unit. As indicated at block 602, a cardiac cycle marker is detected. The accelerometer (such as accelerometer 148) is activated in response to the detected cardiac cycle marker in order to obtain, for example, a measured related to a peak endocardial acceleration (PEA) value as generally noted at block 604. The LCP is optionally configured to provide pacing signals, as generally noted at block 608. The accelerometer is deactivated after obtaining the measure related to the peak endocardial acceleration (PEA) value in order to conserve battery power in the battery, as generally noted at block 606. It will be appreciated that the step indicated at block 608 may occur before or after the deactivation step shown at block 606.

Figure 10:
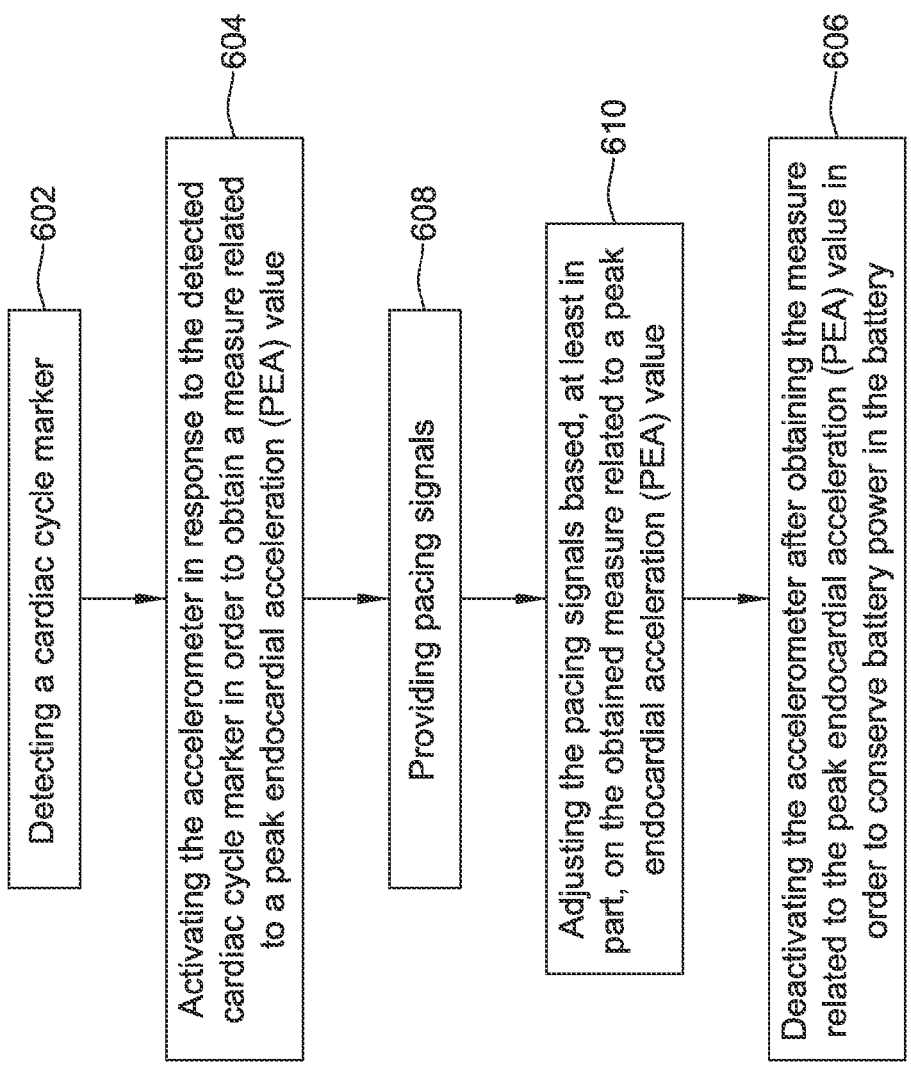
FIG. 10 is a flow diagram of an illustrative method that may be implemented by a medical device such as those illustrated in FIGS. 1-7.

FIG. 10 is a flow diagram showing an illustrative method that may be carried out using an LCP having an accelerometer, a battery and a power management unit. As indicated at block 602, a cardiac cycle marker is detected. The accelerometer (such as accelerometer 148) is activated in response to the detected cardiac cycle marker in order to obtain, for example, a measure related to a peak endocardial acceleration (PEA) value, as generally noted at block 604. The LCP is optionally configured to provide pacing signals, as generally noted at block 608. In some embodiments, and as seen at block 610, the pacing signals are adjusted, based at least in part, upon the obtained measure related to a peak endocardial acceleration (PEA) value. The accelerometer is deactivated after obtaining the measure related to the peak endocardial acceleration (PEA) value in order to conserve battery power in the battery, as generally noted at block 606. It will be appreciated that the steps indicated at blocks 608 and 610 may occur before or after the deactivation step shown at block 606.

While an accelerometer is referenced in FIGS. 8-10, it is contemplated that any suitable sensor may be used (e.g. acoustic sensor, pressure sensor, etc.). Moreover, while peak endocardial acceleration (PEA) is referenced in FIGS. 8-10, it is contemplated that any suitable parameter may be measured (e.g. peak heart sounds, peak pressure, etc.), as each of these provides an indication of how well the heart is beating.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

We claim:

1. A leadless cardiac pacemaker (LCP) configured to sense and pace a patient's heart, the LCP comprising:
   a sensor configured to sense a parameter related to cardiac contractility of the patient's heart;
   a power management unit operatively coupled to the sensor, the power management unit configured to:
      place the sensor in a higher power sense mode during times when sensing the parameter related to cardiac contractility is desired; and
      place the sensor in a lower power mode during times when sensing the parameter related to cardiac contractility is not desired.

2. The leadless cardiac pacemaker (LCP) of claim 1, wherein the sensor comprises an accelerometer.

3. The leadless cardiac pacemaker (LCP) of claim 1, wherein the sensor comprises one or more of an acoustic sensor, an impedance sensor, a flow sensor and a pressure sensor.

4. The leadless cardiac pacemaker (LCP) of claim 1, wherein the power management unit turns the sensor on in the higher power sense mode and turns the sensor off in the lower power mode.

5. The leadless cardiac pacemaker (LCP) of claim 1, wherein the sensor consumes power in the higher power sense mode but does not consume power in the lower power mode.

6. The leadless cardiac pacemaker (LCP) of claim 1, wherein the sensor consumes power in both the higher power sense mode and the lower power mode.

7. The leadless cardiac pacemaker (LCP) of claim 1, wherein the parameter related to cardiac contractility of the patient's heart is related to the peak endocardial acceleration (PEA) of the heart.

8. The leadless cardiac pacemaker (LCP) of claim 1, wherein the power management system:
  receives a cardiac cycle marker;
  places the sensor in the higher power sense mode during a detection window that starts a predetermined time after the cardiac cycle marker; and
  places the sensor in the lower power mode after the detection window.

9. The leadless cardiac pacemaker (LCP) of claim 8, wherein the cardiac cycle marker comprises one or more of a detected R-wave, a pace event and a detected heart sound.

10. The leadless cardiac pacemaker (LCP) of claim 8, wherein the power management system is configured to place the sensor in the higher power sense mode N times for every M cardiac cycle markers, where N is less than M.

11. The leadless cardiac pacemaker (LCP) of claim 10, wherein N and M are dependent upon a patient activity level.

12. The leadless cardiac pacemaker (LCP) of claim 1, further comprising
  a pacing module for pacing the heart at a pacing rate, wherein the pacing rate is dependent, at least in part, on the sensed parameter related to cardiac contractility of the patient's heart.

13. A system comprising:
  a leadless cardiac pacemaker (LCP) including:
    a housing;
    an accelerometer disposed within the housing;
    a controller configured to activate the accelerometer in response to a detected cardiac cycle marker;
    two or more electrodes for receiving conducted communication signals emanating from outside of the housing; and
    a receiver coupled to the two or more electrodes for receiving a communication via conducted communication from outside the housing; and
  an external sensor, remote from the leadless cardiac pacemaker, for detecting a cardiac cycle maker and communicating the marker via conducted communication to the leadless cardiac pacemaker (LCP).

14. The system of claim 13, wherein the external sensor comprises one or more of a pressure sensor, a flow sensor and an impedance sensor.

15. A method of monitoring heart activity using a leadless cardiac pacemaker (LCP), the leadless cardiac pacemaker including an accelerometer, a battery and a power management unit, the method comprising:
  detecting a cardiac cycle marker;
  activating the accelerometer in response to the detected cardiac cycle marker in order to obtain a measure related to a peak endocardial acceleration (PEA) value; and
  deactivating the accelerometer after obtaining the measure related to the peak endocardial acceleration (PEA) value in order to conserve battery power in the battery.

16. The method of claim 15, further comprising providing pacing signals and adjusting the pacing signals based, at least in part, on the obtained measure related to a peak endocardial acceleration (PEA) value.

17. The method of claim 15, wherein detecting a cardiac cycle marker comprises detecting an R-wave.

18. The method of claim 15, wherein the power management unit activates the accelerometer N times for each M detected cardiac cycle markers, where N is less than M.

19. The method of claim 18, further comprising adjusting N and M in accordance with patient activity.

20. The method of claim 15, wherein the power management unit is configured to activate the accelerometer in response to a pace event.

* * * * *